(12) United States Patent
Williamson et al.

(10) Patent No.: US 8,105,272 B2
(45) Date of Patent: Jan. 31, 2012

(54) TRIGGERING MECHANISM FOR A NEEDLE-FREE INJECTOR

(75) Inventors: Daniel E. Williamson, Sherwood, OR (US); Ryan R. Beylund, Milwaukie, OR (US)

(73) Assignee: Bioject, Inc., Tualatin, OR (US)

( * ) Notice: Subject to any disclaimer, the term of this patent is extended or adjusted under 35 U.S.C. 154(b) by 318 days.

(21) Appl. No.: 12/480,561

(22) Filed: Jun. 8, 2009

(65) Prior Publication Data

US 2009/0247940 A1  Oct. 1, 2009

Related U.S. Application Data

(62) Division of application No. 11/539,585, filed on Oct. 6, 2006, now Pat. No. 7,547,293.

(51) Int. Cl.
*A61M 5/30* (2006.01)
(52) U.S. Cl. .......................................................... 604/70
(58) Field of Classification Search .................. 604/131, 604/187, 156, 154, 232, 207, 208, 218, 181, 604/220–222, 225, 228, 230, 236, 134–137, 604/143, 147, 68–70
See application file for complete search history.

(56) References Cited

U.S. PATENT DOCUMENTS

| | | |
|---|---|---|
| 2,545,017 A | 3/1951 | Billingsley |
| 2,582,818 A | 1/1952 | Coby |
| 2,653,602 A | 9/1953 | Smoot |
| 2,667,874 A | 2/1954 | Dickinson, Jr. |
| 2,680,439 A | 6/1954 | Sutermeister |
| 3,110,309 A | 11/1963 | Higgins |
| 3,115,133 A | 12/1963 | Morando |
| 3,202,151 A | 8/1965 | Kath |
| 3,292,621 A | 12/1966 | Banker |
| 3,507,276 A | 4/1970 | Burgess |
| 3,552,083 A | 1/1971 | Andersen et al. |

(Continued)

FOREIGN PATENT DOCUMENTS

EP 0427457 5/1991

(Continued)

OTHER PUBLICATIONS

International Search Report for Application No. PCT/US2007/020254.

(Continued)

*Primary Examiner* — Manuel Mendez
(74) *Attorney, Agent, or Firm* — Schwabe, Williamson & Wyatt, P.C.

(57) ABSTRACT

Needle-free hypodermic jet injection devices having an actuation system to effect an injection from a drug delivery system. The actuation system includes an injection force assembly adapted to transmit a driving force to the drug delivery system. The actuation system further includes a trigger assembly adapted to alter the actuation system between a plurality of configurations including a fired configuration in which the injection force assembly transmits a driving force to the drug delivery system. In some embodiments, the device has a recoil restriction system including a restriction member adapted to couple the recoil restriction system to the trigger assembly and a recoil member coupled to the injection force assembly and movable relative to the restriction member. The restriction member limits movement of the recoil member once the recoil member moves a predetermined distance relative to the restriction member.

13 Claims, 4 Drawing Sheets

U.S. PATENT DOCUMENTS

| | | | |
|---|---|---|---|
| 3,561,443 A | 2/1971 | Banker |
| 3,688,765 A | 9/1972 | Gasaway |
| 3,695,266 A | 10/1972 | Lussier |
| 3,714,943 A | 2/1973 | Yanof et al. |
| 3,729,031 A | 4/1973 | Baldwin |
| 3,853,125 A | 12/1974 | Clark et al. |
| 3,859,996 A | 1/1975 | Mizzy et al. |
| 3,940,003 A | 2/1976 | Larson |
| 3,941,128 A | 3/1976 | Baldwin |
| 3,945,379 A | 3/1976 | Pritz et al. |
| 4,059,107 A | 11/1977 | Iriguchi et al. |
| 4,124,024 A | 11/1978 | Schwebel et al. |
| 4,266,541 A | 5/1981 | Landau |
| 4,447,225 A | 5/1984 | Taff et al. |
| 4,479,801 A | 10/1984 | Cohen |
| 4,560,377 A | 12/1985 | Geat et al. |
| 4,592,745 A | 6/1986 | Rex et al. |
| 4,596,556 A | 6/1986 | Morrow et al. |
| 4,652,261 A | 3/1987 | Mech et al. |
| 4,662,878 A | 5/1987 | Lindmayer |
| 4,680,027 A | 7/1987 | Parsons et al. |
| 4,713,061 A | 12/1987 | Tarello et al. |
| 4,717,384 A | 1/1988 | Waldeisen |
| 4,747,839 A | 5/1988 | Tarello et al. |
| 4,790,824 A | 12/1988 | Morrow et al. |
| 4,850,967 A | 7/1989 | Cosmai |
| 4,886,495 A | 12/1989 | Reynolds |
| 4,909,794 A | 3/1990 | Haber et al. |
| 4,913,699 A | 4/1990 | Parsons |
| 4,940,460 A | 7/1990 | Casey et al. |
| 4,941,880 A | 7/1990 | Burns |
| 5,009,637 A | 4/1991 | Newman et al. |
| 5,024,656 A | 6/1991 | Gasaway et al. |
| 5,049,128 A | 9/1991 | Duquette |
| 5,064,413 A | 11/1991 | McKinnon |
| 5,080,648 A | 1/1992 | D'Antonio |
| 5,135,514 A | 8/1992 | Kimber |
| 5,171,214 A | 12/1992 | Kolber et al. |
| 5,179,024 A | 1/1993 | Dahms |
| 5,181,909 A | 1/1993 | McFarlane |
| 5,273,544 A | 12/1993 | Van der Wal |
| 5,306,277 A | 4/1994 | Bryant et al. |
| 5,318,522 A | 6/1994 | D'Antonio |
| 5,334,144 A | 8/1994 | Alchas et al. |
| 5,364,386 A | 11/1994 | Fukuoka et al. |
| 5,383,851 A | 1/1995 | McKinnon, Jr. et al. |
| 5,393,497 A | 2/1995 | Haber et al. |
| 5,399,163 A | 3/1995 | Peterson et al. |
| 5,453,096 A | 9/1995 | Lataix |
| 5,462,535 A | 10/1995 | Bonnichsen et al. |
| 5,472,022 A | 12/1995 | Michel et al. |
| 5,480,381 A | 1/1996 | Weston |
| 5,499,972 A | 3/1996 | Parsons |
| 5,503,627 A | 4/1996 | McKinnon et al. |
| 5,503,628 A | 4/1996 | Fetters et al. |
| 5,505,697 A | 4/1996 | McKinnon, Jr. et al. |
| 5,520,639 A | 5/1996 | Peterson et al. |
| 5,569,190 A | 10/1996 | D'Antonio |
| 5,573,513 A | 11/1996 | Wozencroft |
| 5,599,302 A | 2/1997 | Lilley et al. |
| 5,645,538 A | 7/1997 | Richmond |
| 5,704,911 A | 1/1998 | Parsons |
| 5,716,348 A | 2/1998 | Marinacci et al. |
| 5,730,723 A | 3/1998 | Castellano et al. |
| 5,746,714 A | 5/1998 | Salo et al. |
| 5,769,138 A | 6/1998 | Sadowski et al. |
| 5,782,802 A | 7/1998 | Landau |
| 5,865,795 A | 2/1999 | Schiff et al. |
| 5,891,085 A | 4/1999 | Lilley et al. |
| 5,891,086 A | 4/1999 | Weston |
| 5,893,397 A | 4/1999 | Peterson et al. |
| 5,911,703 A | 6/1999 | Slate et al. |
| 5,921,967 A | 7/1999 | Sadowski et al. |
| 5,938,637 A | 8/1999 | Austin et al. |
| 5,957,886 A | 9/1999 | Weston |
| 5,993,412 A | 11/1999 | Deily et al. |
| 6,053,890 A | 4/2000 | Moreau Defarges et al. |
| 6,056,716 A | 5/2000 | D'Antonio et al. |
| 6,063,053 A | 5/2000 | Castellano et al. |
| 6,080,130 A | 6/2000 | Castellano |
| 6,096,002 A | 8/2000 | Landau |
| 6,132,395 A | 10/2000 | Landau et al. |
| 6,135,979 A | 10/2000 | Weston |
| 6,149,625 A | 11/2000 | Weston et al. |
| 6,156,008 A | 12/2000 | Castellano |
| 6,168,587 B1 | 1/2001 | Bellhouse et al. |
| 6,174,304 B1 | 1/2001 | Weston |
| 6,179,583 B1 | 1/2001 | Weston |
| 6,210,359 B1 | 4/2001 | Patel et al. |
| 6,216,493 B1 | 4/2001 | Weston et al. |
| 6,223,786 B1 | 5/2001 | Castellano |
| 6,224,567 B1 | 5/2001 | Roser |
| 6,251,091 B1 | 6/2001 | Weston |
| 6,251,099 B1 | 6/2001 | Kollias et al. |
| 6,258,059 B1 | 7/2001 | Weston et al. |
| 6,264,629 B1 | 7/2001 | Landau |
| 6,280,410 B1 | 8/2001 | Weston et al. |
| 6,319,224 B1 | 11/2001 | Stout et al. |
| 6,383,168 B1 | 5/2002 | Landau et al. |
| 6,387,074 B1 | 5/2002 | Horppu et al. |
| 6,406,455 B1 | 6/2002 | Willis et al. |
| 6,409,032 B1 | 6/2002 | Bekkers et al. |
| 6,415,631 B1 | 7/2002 | Weston et al. |
| 6,471,669 B2 | 10/2002 | Landau |
| 6,475,181 B1 | 11/2002 | Potter et al. |
| 6,537,245 B1 | 3/2003 | Alexandre et al. |
| 6,554,818 B2 | 4/2003 | Weston et al. |
| 6,558,348 B2 | 5/2003 | Parsons |
| 6,572,581 B1 | 6/2003 | Landau |
| 6,585,685 B2 | 7/2003 | Staylor et al. |
| 6,607,510 B2 | 8/2003 | Landau |
| 6,610,028 B1 | 8/2003 | Alexandre et al. |
| 6,616,627 B2 | 9/2003 | Willis et al. |
| 6,620,135 B1 | 9/2003 | Weston et al. |
| 6,623,446 B1 | 9/2003 | Navelier et al. |
| 6,623,449 B2 | 9/2003 | Paskar |
| 6,641,554 B2 | 11/2003 | Landau |
| 6,645,170 B2 | 11/2003 | Landau |
| 6,648,850 B2 | 11/2003 | Landau |
| 6,652,483 B2 | 11/2003 | Slate et al. |
| 6,666,843 B1 | 12/2003 | Alexandre et al. |
| 6,673,035 B1 | 1/2004 | Rice et al. |
| 6,673,038 B2 | 1/2004 | Weston |
| 6,676,630 B2 | 1/2004 | Landau et al. |
| 6,681,810 B2 | 1/2004 | Weston |
| 6,682,504 B2 | 1/2004 | Nelson et al. |
| 6,689,093 B2 | 2/2004 | Landau |
| 6,752,780 B2 | 6/2004 | Stout et al. |
| 6,752,781 B2 | 6/2004 | Landau et al. |
| 6,758,829 B2 | 7/2004 | Alexandre et al. |
| 6,783,509 B1 | 8/2004 | Landau et al. |
| 6,835,187 B2 | 12/2004 | Alexandre et al. |
| 6,837,866 B1 | 1/2005 | Alexandre et al. |
| 6,883,222 B2 | 4/2005 | Landau |
| 6,905,475 B2 | 6/2005 | Hauschild et al. |
| 6,911,015 B2 | 6/2005 | Alexandre et al. |
| 6,913,592 B2 | 7/2005 | Parsons |
| 6,913,593 B1 | 7/2005 | Alexandre et al. |
| 6,935,384 B2 | 8/2005 | Landau et al. |
| 6,939,324 B2 | 9/2005 | Gonnelli et al. |
| 6,942,645 B2 | 9/2005 | Alexandre et al. |
| 6,960,184 B2 | 11/2005 | Willis et al. |
| 6,964,650 B2 | 11/2005 | Alexandre et al. |
| 6,979,310 B2 | 12/2005 | Navelier et al. |
| 6,981,961 B1 | 1/2006 | Navelier et al. |
| 7,056,300 B2 | 6/2006 | Alexandre et al. |
| 7,150,409 B2 | 12/2006 | Gonnelli et al. |
| 7,156,822 B2 | 1/2007 | Navelier et al. |
| 7,156,823 B2 | 1/2007 | Landau et al. |
| 7,341,575 B2 | 3/2008 | Rice et al. |
| 7,357,780 B2 | 4/2008 | Alexandre et al. |
| 2001/0002433 A1 | 5/2001 | Weston |
| 2001/0004682 A1 | 6/2001 | Weston |
| 2002/0156418 A1 | 10/2002 | Gonnelli et al. |
| 2003/0149397 A9 | 8/2003 | Gonnelli et al. |
| 2004/0106895 A1 | 6/2004 | Slate et al. |
| 2004/0111054 A1 | 6/2004 | Landau et al. |

| | | | |
|---|---|---|---|
| 2004/0210188 A1 | 10/2004 | Glines et al. | |
| 2004/0215136 A1 | 10/2004 | Navelier et al. | |
| 2004/0215137 A1 | 10/2004 | Navelier et al. | |
| 2004/0220525 A1 | 11/2004 | Willis et al. | |
| 2004/0254526 A1 | 12/2004 | Weston | |
| 2005/0010167 A1 | 1/2005 | Alexandre et al. | |
| 2005/0119618 A1 | 6/2005 | Gonnelli | |
| 2005/0154350 A1 | 7/2005 | Willis et al. | |
| 2005/0192530 A1 | 9/2005 | Castellano | |
| 2005/0209554 A1 | 9/2005 | Landau | |
| 2005/0267403 A1 | 12/2005 | Landau et al. | |
| 2006/0069345 A1 | 3/2006 | Anderson et al. | |
| 2006/0089594 A1 | 4/2006 | Landau | |
| 2006/0089595 A1 | 4/2006 | Alexandre et al. | |
| 2006/0189927 A1 | 8/2006 | Alexandre et al. | |
| 2006/0247573 A1 | 11/2006 | Alexandre et al. | |

FOREIGN PATENT DOCUMENTS

| | | |
|---|---|---|
| NL | 133435 | 2/1972 |
| WO | WO9737705 | 10/1997 |
| WO | WO9852632 | 11/1998 |
| WO | WO0033899 | 6/2000 |
| WO | WO0048654 | 8/2000 |
| WO | WO0113975 | 3/2001 |
| WO | WO0137906 | 5/2001 |
| WO | WO03103752 | 12/2003 |

OTHER PUBLICATIONS

Written Opinion of the International Searching Authority for Application No. PCT/US2007/020254.

"Zogenix Intraject® Webpage," Copyright 2007, at http://www.zogenix.com/products.html, printed Feb. 12, 2007.

"Zogenix DosePro Webpage," Copyright 2008, at http://www.zogenix.com/index.php/products/sumatriptandosepro/, printed Jul. 9, 2008.

"Schott Ampoules made of Glass Webpage," Copyright 2007, at http://www.us.schott.com/pharmaceutical_packaging/english/products/ampules/index.html, printed Jun. 26, 2007.

"BioValve Mini-Ject Webpage," at http://www.biovalve.com/products/miniject.shtml, printed Feb. 12, 2007.

"Pages from Crossject Website," at http://www.crossject.com/, printed Feb. 12, 2007.

International Preliminary Report on Patentability for Application No. PCT/US2007/018853.

International Search Report for Application No. PCT/US2007/018853.

Written Opinion of the International Searching Authority for Application No. PCT/US2007/018853.

TRIGGERING MECHANISM FOR A NEEDLE-FREE INJECTOR

RELATED APPLICATION

This application is a divisional application of and claims priority to U.S. patent application Ser. No. 11/539,585, entitled "Triggering Mechanism For Needle-Free Injector," which was filed Oct. 6, 2006, and which issued Jun. 16, 2009 as U.S. Pat. No. 7,547,293, the complete disclosure of which is incorporated herein by reference for all purposes.

BACKGROUND

Needle-free injection systems provide an alternative to standard fluid delivery systems, which typically use a needle adapted to penetrate the outer surface of a target. Typically, needle-free injection systems are designed to eject the fluid from a fluid chamber with sufficient pressure to allow the fluid to penetrate the target to the desired degree. For example, common applications for needle-free injection systems include delivering intradermal, subcutaneous, and intramuscular injections into or through a recipient's skin. For each of these applications, the fluid must be ejected from the system with sufficient pressure to allow the fluid to penetrate the tough exterior dermal layers of the recipient's skin.

Examples of needle-free injection systems are found in U.S. Pat. Nos. 4,940,460, 4,941,880, 5,399,163, 5,746,714, 5,782,802, 5,993,412, 6,096,002, 6,132,395, 6,264,629, 6,383,168, 6,471,669, 6,572,581, 6,585,685, 6,607,510, 6,641,554, 6,645,170, 6,648,850, 6,676,630, 6,689,093, 6,752,781, and 6,783,509, the disclosures of which are incorporated herein by reference for all purposes.

Since needle-free injection systems require the production of high fluid pressures, recoil of injector components may limit device accuracy or effectiveness. Various attempts have therefore been made to reduce recoil in injection systems. Examples of such devices are found in U.S. Pat. No. 5,957,886 and U.S. Patent Application Nos. 2004/0106895 and 2005/0267403, the disclosures of which are incorporated herein by reference for all purposes.

SUMMARY

The present disclosure is directed to needle-free injection devices having actuation systems to effect an injection. The devices have a drug delivery system including a nozzle having a drug chamber and an outlet orifice. The drug delivery system is adapted to expel a volume of liquid from the drug chamber through the outlet orifice at a sufficient pressure to penetrate a recipient's skin.

The devices also have an actuation system that includes an injection force assembly adapted to transmit a driving force to the drug delivery system. The actuation system further includes a trigger assembly adapted to alter the actuation system between a plurality of configurations including a fired configuration in which the injection force assembly transmits a driving force to the drug delivery system. In some embodiments, the device has a recoil restriction system including a restriction member adapted to couple the recoil restriction system to the trigger assembly and a recoil member coupled to the injection force assembly and movable relative to the restriction member. The restriction member limits movement of the recoil member once the recoil member moves a predetermined distance relative to the restriction member.

The advantages of the disclosed needle-free injector may be understood more readily after a consideration of the drawings and the Detailed Description.

DETAILED DESCRIPTION

FIGS. 1-7 illustrate exemplary needle-free injection devices 10. Although the disclosed devices are intended to be single-use, disposable devices, various aspects of the devices may be incorporated into reusable needle-free injectors.

Device 10 may include one or more systems to effect an injection. For example, the device of FIGS. 1-3 includes a drug delivery system 12, an actuation system 14, and a recoil restriction system 16. Drug delivery system 12 provides an interface for delivery of a drug to a recipient and expels a volume of liquid from the device. Actuation system 14 provides a driving force to the drug delivery system. Recoil restriction system 16 limits effects of recoil upon actuation, or firing, of the device.

Figure 1:
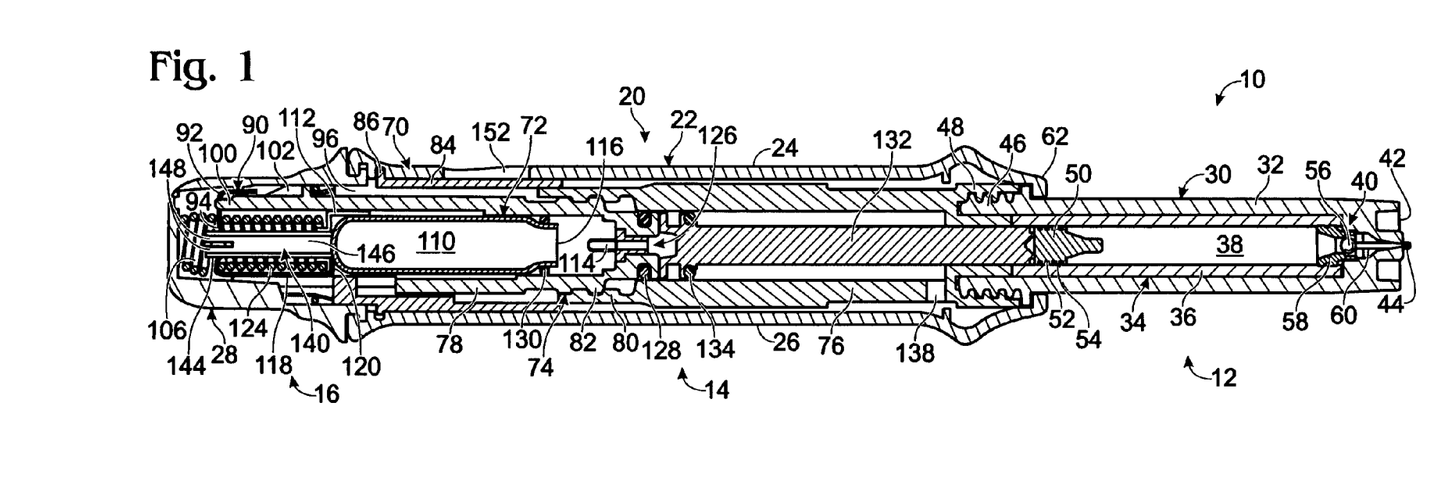
FIG. 1 is a cross-sectional view of an exemplary device in a stored configuration in which a drug chamber is not in fluid communication with an outlet orifice of the device.
Figure 2:
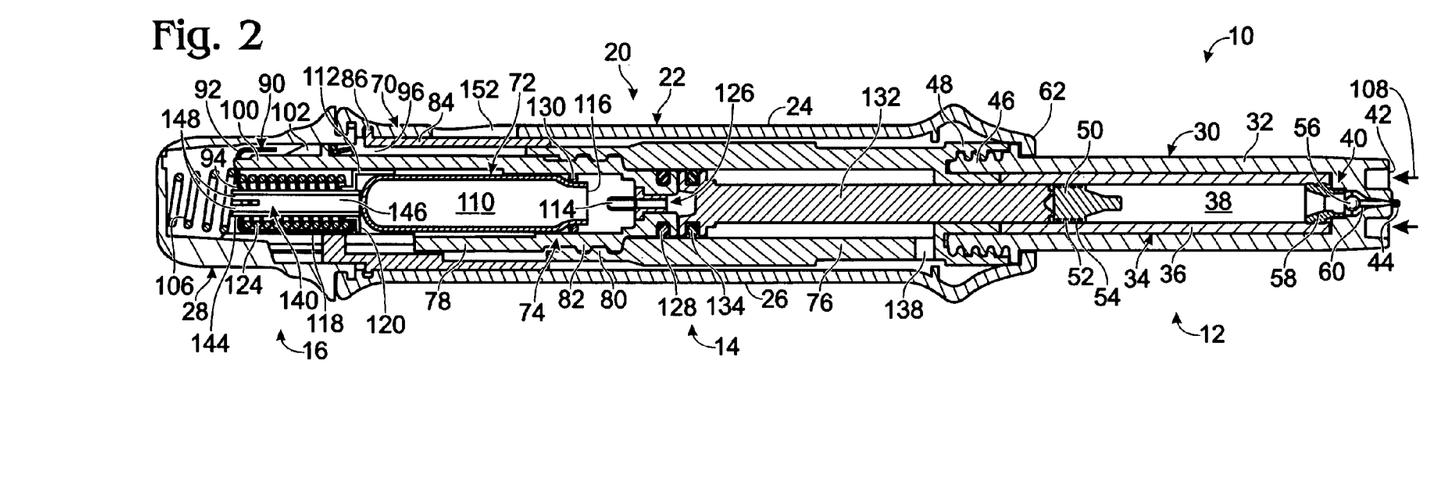
FIG. 2 is a cross-sectional view of the exemplary device of FIG. 1 in a primed configuration in which the drug chamber is in fluid communication with the outlet orifice.
Figure 3:
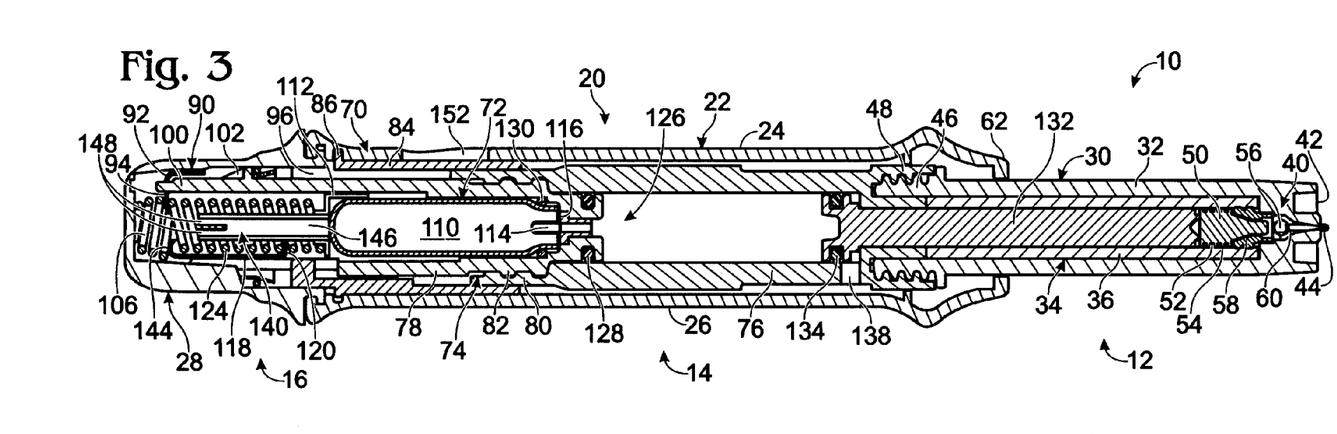
FIG. 3 is a cross-sectional view of the exemplary device of FIGS. 1 and 2 in a fired configuration in which an injection force assembly transmits a driving force to a drug delivery system to expel a drug from the drug chamber through the outlet orifice.

Device 10 includes a body 20 to house the various systems. As shown in FIGS. 1-3, body 20 includes an outer housing 22 configured to house actuation system 14 and recoil restriction system 16. The body is also configured to receive drug delivery system 12 for delivery of a drug or other fluid into a recipient. The outer housing may include a top 24 and a bottom 26 for ease of assembly of the device. Body 20 further includes a back cover 28, which is configured to move relative to outer housing 22. Body 20 is typically configured to be comfortably held in a user's hand and may take any suitable configuration. Body 20 may be formed from injection-molded plastic, though various other materials and fabrication methods may be suitable.

Drug delivery system 12 is configured to expel a volume of fluid, such as a drug, from the device. The word "drug" as used herein is intended to encompass, for example, and without limitation, any medication, pharmaceutical, therapeutic, vaccine, or other material which can be administered by injection. In a single-use configuration, the drug delivery system may be permanently retained in, or coupled to, body 20 prior to providing the device to a user; however, it should be appreciated that drug delivery system 12 may be selectively engageable with the remainder of the device, such as for reusable devices.

Drug delivery system 12 includes a nozzle 30 in the form of a plastic sleeve 32. Nozzle 30 may be filled during operation of the device or may include a pre-filled drug injection cartridge 34 placed within the plastic sleeve. As shown in the exemplary device of FIGS. 1-3, drug cartridge 34 includes a glass sleeve 36 which forms a drug chamber 38. The glass sleeve terminates adjacent an outlet valve 40 that communicates with an end surface 42 of the nozzle 30 through an outlet orifice 44. Outlet orifice 44 is shown in the form of a fine-dimension opening from which issues a high velocity jet of medication upon actuation of the device.

In the exemplary device, drug delivery system 12 is coupled to actuation system 14. As illustrated in FIGS. 1-3, coupling threads 46, 48 join the nozzle and the actuation system. For single-use devices, these threaded sections may be joined prior to assembly of outer housing 22 to prevent reuse of the device.

Although the depicted example illustrates a drug chamber having constant diameter, the walls of the drug chamber may take the form of a stepped-through bore having various diameters along the length of the cartridge, such as shown in U.S. Pat. No. 6,264,629. For example, the glass sleeve may be contoured to provide for variation in diameter.

Sealingly and movably received in drug chamber 38 is a resilient plunger 50. The plunger may include multiple grooves 52 interdigitated with sealing ribs 54 that engage the walls of the drug chamber 38. Movement of plunger 50 urges fluid out of drug chamber 38 through outlet orifice 44.

Outlet valve 40 is formed by a plug member 56 that moves from being held by a drug cartridge seal 58 to a plug receiving chamber 60. As described in U.S. Pat. No. 6,264,629, the disclosure of which is incorporated in its entirety, receiving chamber 60 may include one or more channels through which fluid may bypass the plug member so that the drug chamber is in fluid communication with the outlet orifice once the plug member has moved into the receiving chamber. Alternatively, or additionally, plug member 56 may include ribs or slots, such as described in U.S. Pat. No. 6,132,395, to provide bypass channels for fluid communication between the drug chamber and the outlet orifice.

Prior to its use to effect an injection, outlet orifice 44 of the pre-filled drug cartridge may be sealed by placing a peel-off type of sealing membrane over end surface 42, which may be formed, for example, of foil or of a polymer/paper laminate as are conventional and well known in the art.

In some versions of the device, such as shown in FIGS. 1-3, outer housing 22 includes a lip 62 to limit movement of the drug delivery system within the housing. For example, lip 62 may provide an end point for movement of the drug delivery system within the housing during assembly of the device and firing of the device, such as upon recoil.

Actuation system 14 provides a driving force to the drug delivery system and is alterable between a plurality of configurations. For example, actuation system 14 has a stored configuration in which the drug chamber is not in fluid communication with the outlet orifice, such as through placement of plug member 56 within cartridge seal 58, as shown in FIG. 1. FIG. 2 illustrates actuation system 14 in a primed configuration in which the drug chamber is in fluid communication with the outlet orifice. As will later be described, movement of plunger 50 may urge plug member 56 into receiving chamber 60 to allow fluid to bypass the plug member and thereby exit the drug chamber through the outlet valve. FIG. 3 illustrates the actuation system of an exemplary device in the fired configuration. In the fired configuration, a driving force is transmitted to the drug delivery system to effect an injection, such as by moving plunger 50 to urge the contents of the drug chamber through the outlet orifice.

To alter the actuation system between the plurality of configurations, device 10 includes a trigger assembly 70. Trigger assembly 70 operatively couples actuation system 14 with drug delivery system 12. For example, trigger assembly 70 may control triggering of an injection force assembly 72, which transmits a driving force to the drug delivery system.

In the exemplary device of FIGS. 1-3, trigger assembly 70 comprises an interior housing 74 that couples the actuation system with the drug delivery system. In some versions of the device, interior housing 74 includes selectively engageable first and second housings, such as a forward interior housing 76 and a rearward interior housing 78. The housings move selectively relative to one another to alter the actuation system between at least two of the plurality of configurations, such as from the stored configuration to the primed configuration. As illustrated in FIGS. 1 and 2, housings 76, 78 include thread sections 80 and 82, respectively, that engage one another and may be used to move the forward and rearward interior housings relative to one another.

In the exemplary device of FIGS. 1-4, trigger assembly 70 includes a trigger sleeve 84 to limit relative movement between the forward and rearward interior housings. For example, the trigger sleeve may limit movement between the housings so that alteration of the actuation system between the primed configuration and the stored configuration is limited. Trigger sleeve 84 may include protrusions 86, such as the angled ribs or ratchet teeth shown in the exemplary device of FIG. 5, to limit relative movement between the housings in a predetermined direction. As illustrated, the protrusions extend into the body, such as into outer housing 22, and limit relative movement of the trigger sleeve.

Figure 5:
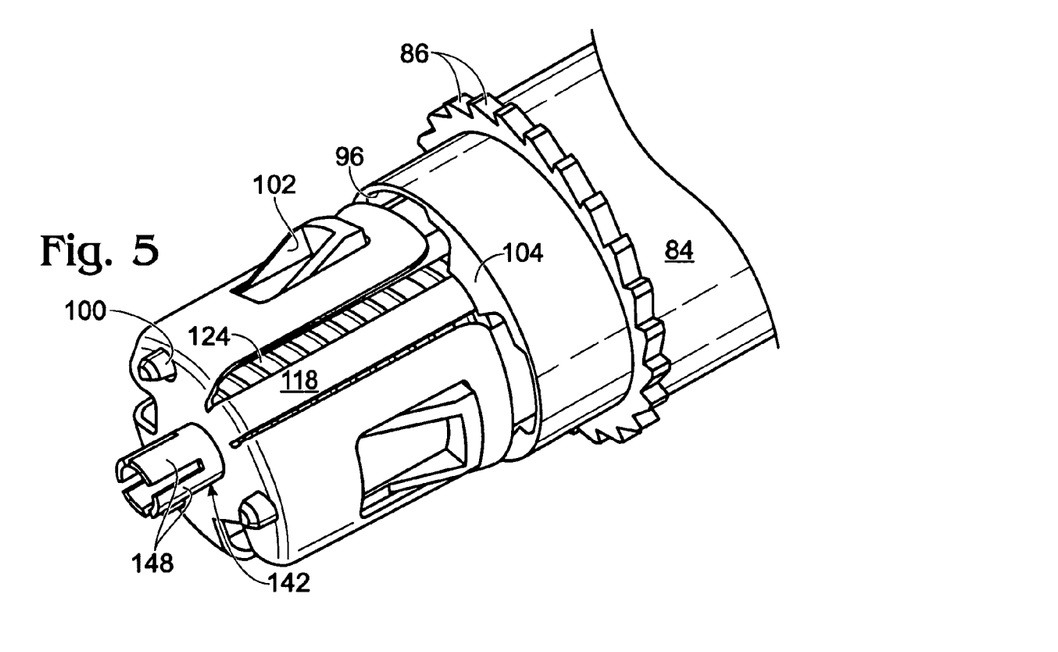
FIG. 5 is a perspective view of an exemplary trigger assembly suitable for the device of FIG. 4, including a retaining member, a recoil member and a trigger sleeve.
Figure 6:
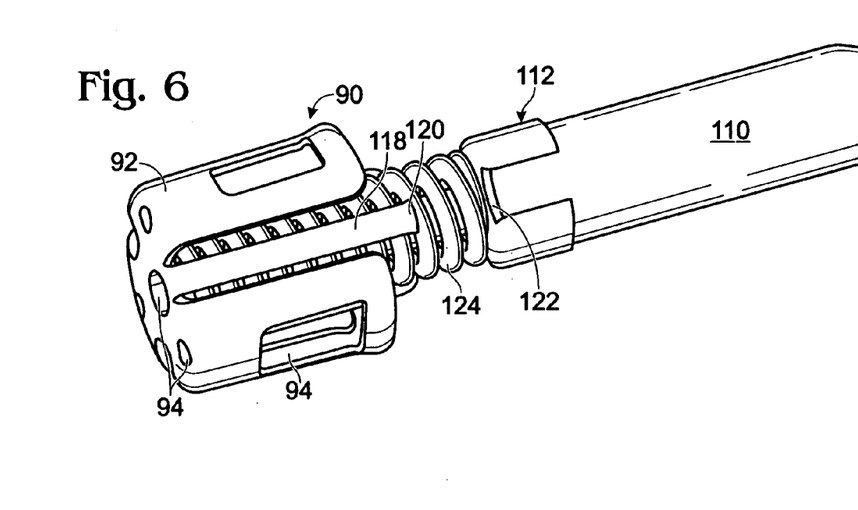
FIG. 6 is a perspective view of the trigger assembly of FIG. 5 with the trigger sleeve removed and the retaining member and recoil member in a fired configuration.
Figure 7:
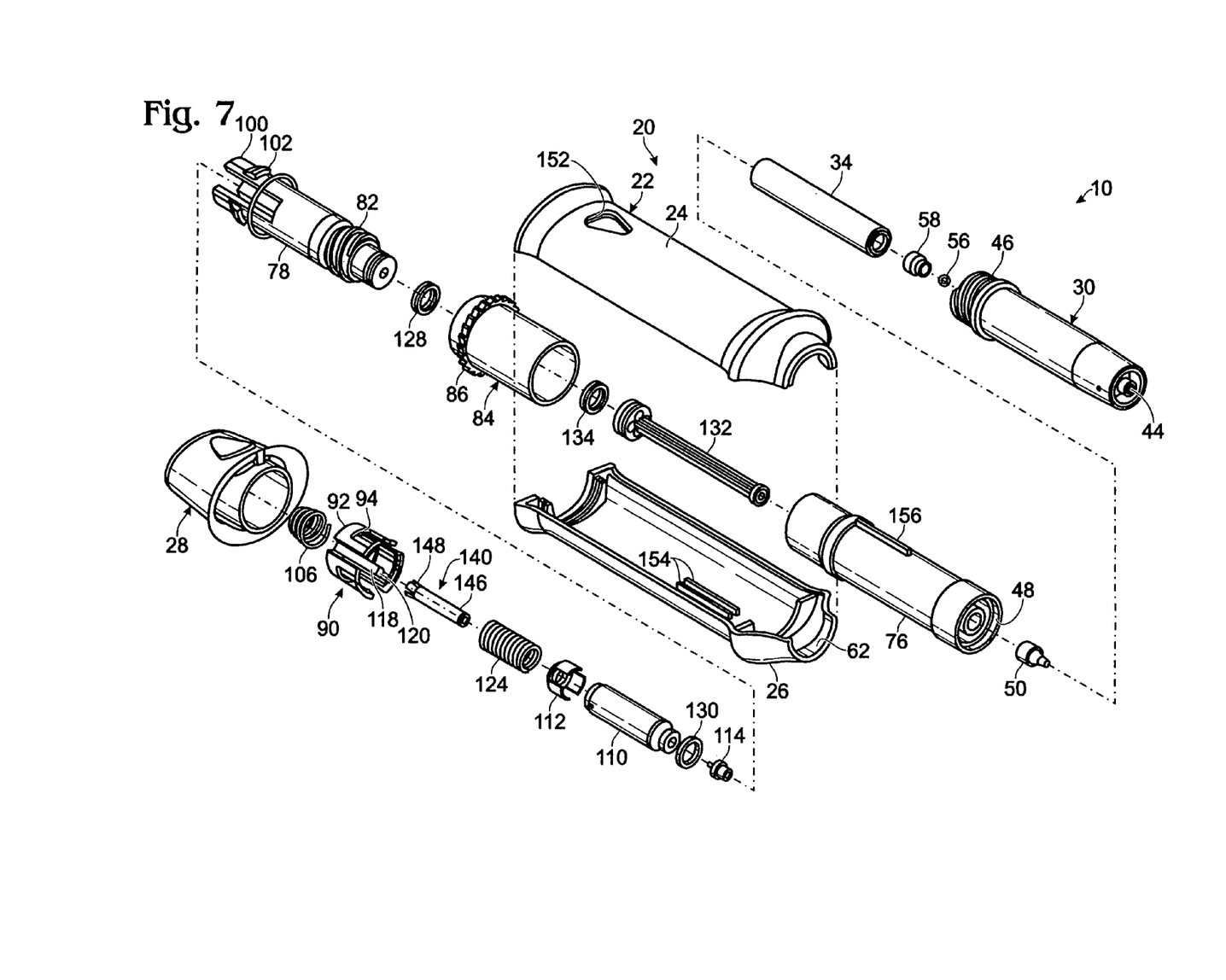
FIG. 7 is an exploded view of the exemplary device of FIGS. 1-6.

As illustrated in FIG. 5, trigger assembly 70 includes a retaining member 90 to limit activation of the injection force assembly. For example, retaining member 90 may be configured to limit transmission of a driving force when the actuation system is in the stored and primed configurations. Retaining member 90 may take the form of a back clip 92 that includes apertures 94, at least some of which are configured to engage with interior housing 74.

Movement of trigger sleeve 84 may be coupled to interior housing 74 and retaining member 90. For example, trigger sleeve 84 includes channels 96 configured to couple movement of the trigger sleeve with one of the interior housings. As shown in FIG. 5, interior rearward housing 78 includes flanges 100 that pass through apertures 94 in back clip 92. Protrusions 102 extend from the flanges to maintain engagement with back clip 92. The trigger sleeve maintains engagement with the rearward interior housing via channels 96 within the trigger sleeve, through which the interior rearward housing translates. Between channels 96 are lips 104 that rest between the flanges of the rearward housing. The trigger sleeve therefore rotates in tandem with the rearward housing and back clip, but allows the rearward housing and back clip to translate independently of the trigger sleeve. Although the components of trigger assembly 70, such as rearward housing flanges 100 and trigger sleeve channels 96 are shown in triplet, any suitable quantity and configuration may be used.

Trigger assembly 70 may be biased against firing of the device, such as by restricting movement of the actuation system to the fired configuration. For example, trigger assembly 70 may include a trigger spring 106 that maintains retaining member 90 away from back cover 28. In some versions of the device, the trigger spring may be tuned to match the magnitude of an axial force 108 of a predetermined value applied to the end of the device, as shown in FIG. 2. Trigger spring 106 may therefore counteract an initial contact force applied to the device as the device is pressed against a recipient's skin. Consequently, a predetermined axial force is necessary to actuate the device to deliver an injection.

Injection force assembly 72 of actuation system 14 transmits a driving force to the drug delivery system. In the exemplary device of FIGS. 1-6, injection force assembly 72 includes a source of pressurized gas, such as gas cartridge 110, to transmit a driving force to the drug delivery system. The injection force assembly includes a hammer member 112 to engage gas cartridge 110 with the drug delivery system by urging gas cartridge 110 towards a pierce pin 114. Pierce pin 114 punctures a penetrable wall 116 of the gas cartridge to release the pressurized gas. In the exemplary device of FIGS. 1-7, device 10 uses pressurized gas supplied from a cartridge to expel fluid from the injection device. However, the pressurized gas may be supplied from a tank or other source. In some versions of device 10, the driving force may be supplied from one or more springs as is known in the art.

Figure 4:
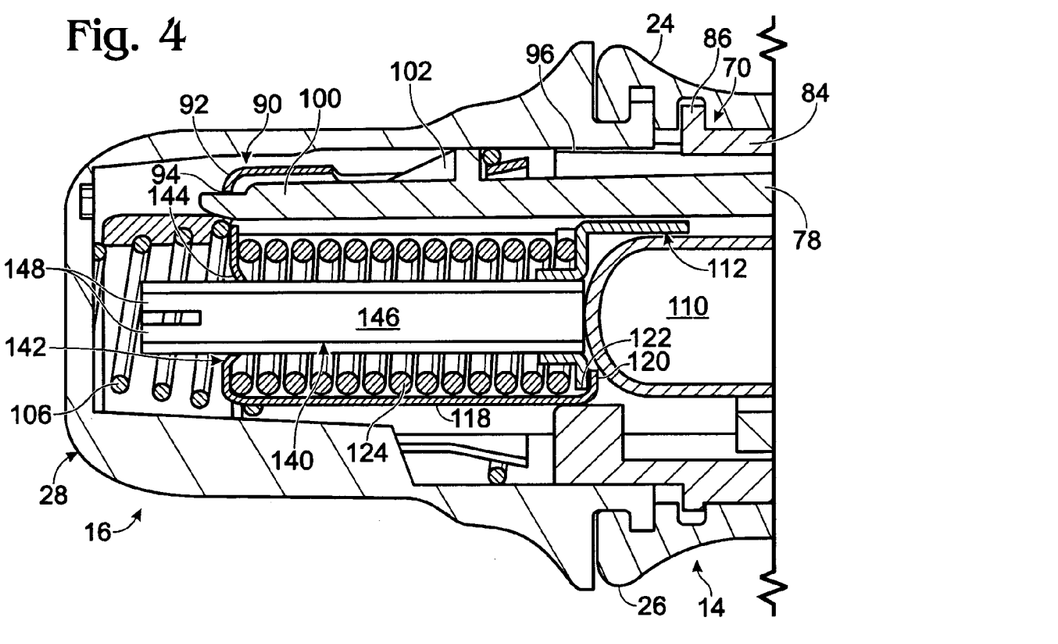
FIG. 4 is a fragmentary cross-sectional view of the exemplary device of FIG. 1 showing details of a recoil restriction system and an actuation system that includes a trigger assembly and an injection force assembly.

In the exemplary device of FIGS. 1-6, retaining member 90 includes extensions 118 ending in detents 120 adapted to releasably couple with injection force assembly 72. For example, detents 120 may be configured to releasably couple with hammer member 112, such as at hammer notches 122. As shown in FIG. 4, the detents may take the form of one or more short, bended tips extending from the retaining member. The detents may have any angle relative to the extensions as is suitable for coupling with the hammer member. A hammer spring 124 is positioned between the retaining member and the hammer member. When detents 120 disengage from notches 122, the hammer spring propels the hammer away from the retaining member to urge the gas cartridge towards the pierce pin. Consequently, the material from which the retaining member is formed and the configuration of the detents may be selected to provide suitable resistance against application of an axial force to, and resulting actuation of, the device.

Gas chamber 126 is formed by forward housing 76. As illustrated in FIGS. 1-3, a seal 128 is provided around rearward interior housing 78 so that pressurized gas from cartridge 110 flows into gas chamber 126 instead of escaping between the interior housings 76, 78. A seal 130 may also be provided adjacent penetrable wall 116 to limit back flow of pressurized gas into rearward housing 78. Located within the forward housing 76 is a gas piston 132 which abuts plunger 50. As pressurized gas is released from cartridge 110, piston 132 is urged into nozzle 30. The plunger is consequently urged along the drug chamber to effect an injection. A seal 134 is provided with piston 132 to limit flow of pressurized gas out of the gas chamber until sufficient movement of the piston has occurred. For example, the interior walls of the rearward housing 78 may include a ridged region near the nozzle to allow venting of excess gas past the piston once the piston has moved to the end of the gas chamber opposite the pierce pin. Gas chamber 126 may include a vent 138 to dissipate excess pressurized gas. Additional vents may be provided in the outer housing to release this exhaust gas or the exhaust gas may be redirected for use in a marking system, such as that described in U.S. Pat. No. 6,676,630.

Recoil restriction system 16 limits effects of recoil once the device is fired, such as by limiting movement of the injection force assembly 72, such as backwards movement of the gas cartridge. Movement of the injection force assembly relative to body 20 may be accomplished by coupling the injection force assembly to the trigger assembly. Consequently, the recoil restriction system may limit movement of the injection force assembly when the actuation system is in the fired configuration.

As illustrated in FIGS. 1-6, recoil restriction system 16 includes a recoil member 140 having a first end coupled to hammer member 112 and a second end configured to engage with retaining member 90. The recoil restriction system also includes a restriction member 142 to couple the recoil restriction system to trigger assembly 70. As shown in FIGS. 1-6, the recoil member is movable relative to the restriction member; however, the restriction member limits movement of the recoil member once the recoil member moves a predetermined distance relative to the restriction member.

In the exemplary device of FIGS. 1-7, restriction member 142 comprises a beveled edge 144 surrounding one of apertures 94 in retaining member 90 through which the recoil member translates. Recoil member 140 comprises an elongate tube 146 coupled to the hammer member and configured to translate through the aperture 94 in the retaining member. In some versions of device 10, the recoil member includes flanges 148 extending from tube 146 to engage with beveled edge 144. Consequently, once the device is fired, the hammer spring urges the hammer and the recoil member away from the retaining member. The recoil member is moved completely through the aperture and is unable to move in the opposite direction since flanges 148 catch on beveled edge 144.

In some versions of device 10, the device may provide feedback or instructions to a user of the device. In the exemplary device of FIGS. 1-3 and 7, the device includes view port 152 in outer housing 22. The view port may be an aperture or window configured to allow a user to view a portion of an interior component, such as trigger sleeve 84, through the outer housing. For example, indicia, such as arrows or text, may instruct a user in proper operation of the device or convey information to a user, such as whether the device is in the stored or primed configuration.

Device 10 may include various mechanisms to restrict undesirable movement of components. For example, in the illustrative device of FIG. 7, outer housing 22 and interior forward housing 76 include one or more ribs 154, 156 that restrict rotation of the outer housing relative to the interior forward housing. For example, outer housing top 24 and/or outer housing bottom 26 may include a pair of ribs that straddle one or more ribs extending from interior forward housing 76. Other suitable mechanisms, such as latches, detents, glues, and the like, may be used to restrict movement between these components and any other components depending on the particular configuration of device 10.

During use, a user primes the device by rotating back cover 28 relative to outer housing 22. As shown in FIGS. 1-4, the lower interior of back cover 28 engages back clip 92 adjacent extensions 118. The back clip 92, interior rearward housing 78, and trigger sleeve 84 therefore rotate with the back cover to thread the rearward housing fully into the interior forward housing 76. Protrusions 86 on trigger sleeve 84 prevent back rotation. Threading of the interior rearward housing into the interior forward housing moves gas piston 132 and plunger 50 towards the outlet orifice to urge plug member 56 into its receiving chamber 60 so that the bypass channels through the nozzle orifice allow fluid flow.

Once the device has been altered from the stored configuration, as demonstrated by FIG. 1, to the primed configuration, as demonstrated by FIG. 2, the device is ready to be used to deliver an injection. The end surface of the nozzle is placed against the skin of the person or animal who is to receive the injection and an axial force is applied to the device, similar to that of the devices describe in U.S. Pat. Nos. 6,096,002 and 6,264,629. The axial force causes the outer housing, back cover, and trigger sleeve to translate relative to the interior components. Accidental firing of the device is resisted by trigger spring 106. When the back cover contacts the end of recoil tube 146, the recoil tube urges hammer member 112 away from back clip 92, thereby releasing detents 120 from the hammer. Hammer spring 124 urges the hammer away from the back clip and propels gas cartridge 110 onto pierce pin 114, thereby moving the piston member and plunger through the drug chamber to effect the injection.

Although the present device has been shown and described with reference to the foregoing operational principles and preferred embodiments, it will be apparent to those skilled in the art that various changes in form and detail can be made without departing from the spirit and scope of the invention. The present invention is intended to embrace all such alternatives, modifications and variances. The subject matter of the present invention includes all novel and non-obvious combinations and subcombinations of the various elements, features, functions and/or properties disclosed herein. Inventions embodied in various combinations and subcombinations of features, functions, elements, and/or properties may be claimed through presentation of claims in a subsequent application.

What is claimed is:

1. A needle-free injection device comprising:
    a drug delivery system including a nozzle having a drug chamber and an outlet orifice, the drug delivery system adapted to expel a volume of liquid from the drug chamber through the outlet orifice;
    an actuation system including:
        an injection force assembly comprising a source of pressurized gas adapted to transmit a driving force to the drug delivery system, and a spring-driven hammer member adapted to engage the source of pressurized gas with the drug delivery system by urging the source of pressurized gas towards a pierce pin to release the pressurized gas;
        a trigger assembly adapted to operatively couple the actuation system with the drug delivery system, the trigger assembly including a retaining member adapted to limit activation of the injection force assembly; and
        a recoil restriction system adapted to limit movement of the injection force assembly and including a recoil member having a first end coupled to the hammer member and a second end adapted to engage with the retaining member.

2. The device of claim 1, wherein the recoil restriction system further includes a restriction member adapted to limit movement of the recoil member and comprising a beveled edge formed around an aperture in the retaining member through which the recoil member passes.

3. The device of claim 2, wherein the recoil member includes flanges adapted to engage with the beveled edge.

4. The device of claim 1, wherein the retaining member includes detents adapted to releasably couple with the hammer member.

5. The device of claim 1, wherein the trigger assembly further includes first and second housings adapted to move selectively relative to one another to alter the actuation system between a stored configuration in which the drug chamber is not in fluid communication with the outlet orifice, and a primed configuration in which the drug chamber is in fluid communication with the outlet orifice.

6. The device of claim 5, wherein the trigger assembly further includes a trigger sleeve adapted to limit movement of the first and second housings from the primed configuration to the stored configuration.

7. The device of claim 6, wherein the trigger sleeve includes protrusions adapted to limit relative movement between the first and second housings in a predetermined direction.

8. A needle-free injection device comprising:
    a drug delivery system including a nozzle having a drug chamber and an outlet orifice, the drug delivery system adapted to expel a volume of liquid from the drug chamber through the outlet orifice;
    an actuation system including:
        an injection force assembly adapted to transmit a driving force to
    the drug delivery system; and
        a trigger assembly adapted to alter the actuation system between a plurality of configurations including a fired configuration in which the injection force assembly transmits a driving force to the drug delivery system, wherein the trigger assembly includes selectively engageable first and second interior housings adapted to couple the actuation system with the drug delivery system, and a trigger sleeve adapted to limit relative movement between the first and second housings; and
    a body configured to house the drug delivery system and the actuation system, the body including:
        an outer housing configured to receive the drug delivery system, and
        a back cover configured to rotatably couple with the outer housing, wherein rotation of the back cover and the trigger sleeve is coupled and axial movement between the back cover and the outer housing is restricted.

9. The device of claim 8, wherein the trigger sleeve includes protrusions extending into the body and configured to limit movement of the trigger sleeve relative to the body and channels configured to couple movement of the trigger sleeve with one of the first and second housings.

10. The device of claim 8, wherein the plurality of configurations further includes a stored configuration in which the drug chamber is not in fluid communication with the outlet orifice and a primed configuration in which the drug chamber is in fluid communication with the outlet orifice, and the trigger assembly includes a retaining member adapted to limit transmission of a driving force when the actuation system is in the stored and primed configurations.

11. The device of claim 10, wherein the retaining member includes detents adapted to releasably couple with the injection force assembly.

12. The device of claim 8, wherein the trigger assembly includes a trigger spring biased to restrict alteration of the actuation system to the fired configuration in response to an axial force less than a predetermined magnitude.

13. The device of claim 8, wherein the device further comprises a recoil restriction system including a recoil member coupled to the injection force assembly, the recoil restriction system adapted to limit movement of the injection force assembly when the actuation system is in the fired configuration.

* * * * *

UNITED STATES PATENT AND TRADEMARK OFFICE
CERTIFICATE OF CORRECTION

PATENT NO. : 8,105,272 B2  
APPLICATION NO. : 12/480561  
DATED : January 31, 2012  
INVENTOR(S) : Daniel E. Williamson et al.

Page 1 of 1

It is certified that error appears in the above-identified patent and that said Letters Patent is hereby corrected as shown below:

In the Claims

Column 8

Line 16-20, "…including:
an injection force assembly adapted to transmit a driving
    force to
the drug delivery system; and
a trigger assembly adapted to…"

should read -- including:
    an injection force assembly adapted to transmit a driving force to
the drug delivery system; and
a trigger assembly adapted to… --.

Signed and Sealed this
Third Day of September, 2013

Teresa Stanek Rea
*Acting Director of the United States Patent and Trademark Office*